United States Patent
Freitag

(10) Patent No.: US 7,785,360 B2
(45) Date of Patent: Aug. 31, 2010

(54) INSTRUMENT FOR IMPLANTING VASCULAR PROSTHESES

(75) Inventor: Lutz Freitag, Hemer (DE)

(73) Assignee: Merit Medical Systems, Inc., South Jordan, UT (US)

( * ) Notice: Subject to any disclaimer, the term of this patent is extended or adjusted under 35 U.S.C. 154(b) by 1004 days.

(21) Appl. No.: 10/491,210

(22) PCT Filed: May 18, 2002

(86) PCT No.: PCT/DE02/01795

§ 371 (c)(1), (2), (4) Date: Jun. 3, 2004

(87) PCT Pub. No.: WO03/034943

PCT Pub. Date: May 1, 2003

(65) Prior Publication Data

US 2004/0249433 A1 Dec. 9, 2004

(30) Foreign Application Priority Data

Sep. 28, 2001 (DE) ................. 101 48 185

(51) Int. Cl.
*A61F 2/06* (2006.01)
(52) U.S. Cl. ..................... 623/1.11; 606/108
(58) Field of Classification Search ............... 623/1.11, 623/1.12, 903; 606/108
See application file for complete search history.

(56) References Cited

U.S. PATENT DOCUMENTS

| 3,196,876 A | 7/1965 | Roberts et al. |
| 4,580,568 A | 4/1986 | Gianturco |
| 4,606,330 A | 8/1986 | Bonnet |
| 4,893,623 A | 1/1990 | Rosenbluth |
| 4,990,151 A * | 2/1991 | Wallsten .................. 606/108 |
| 5,019,085 A | 5/1991 | Hillstead |

(Continued)

FOREIGN PATENT DOCUMENTS

DE 42 40 177 A1 6/1994

(Continued)

OTHER PUBLICATIONS

Office Action in EP1429684 dated Feb. 4, 2008.

(Continued)

*Primary Examiner*—Michael J Milano
*Assistant Examiner*—Victor X Nguyen
(74) *Attorney, Agent, or Firm*—Stoel Rives LLP

(57) ABSTRACT

An instrument for implanting an expandable cylindrical vascular prosthesis includes an outer tube and an inner tube which can be displaced relative to one another. The inner tube is longitudinally slotted on the distal end, at least in an area thereof, and ensheathes the stent with this area which includes the longitudinal slot. In order to implant the stent, the outer tube is retracted. The stent then expands with continuous retracting movement of the outer tube and the inner tube is pressed open along the longitudinal slot. Implantation is terminated, when the outer tube is retracted along the entire length of the stent. The implantation is reversible by pushing the outer tube forward, as long as the stent has not yet fully exited the instrument. In this way, the inner tube is constricted together with the stent, and compressed to an initial position.

14 Claims, 2 Drawing Sheets

U.S. PATENT DOCUMENTS

| | | | |
|---|---|---|---|
| 5,158,548 A | 10/1992 | Lau et al. | |
| 5,159,920 A | 11/1992 | Condon et al. | |
| 5,201,901 A | 4/1993 | Harada et al. | |
| 5,249,585 A | 10/1993 | Turner et al. | |
| 5,290,295 A | 3/1994 | Querals et al. | |
| 5,320,617 A | 6/1994 | Leach | |
| 5,409,453 A | 4/1995 | Lundquist et al. | |
| 5,464,408 A * | 11/1995 | Duc | 606/108 |
| 5,464,449 A | 11/1995 | Ryan | |
| 5,514,093 A | 5/1996 | Ellis et al. | |
| 5,549,644 A | 8/1996 | Lundquist et al. | |
| 5,588,949 A | 12/1996 | Taylor et al. | |
| 5,601,591 A | 2/1997 | Edwards et al. | |
| 5,603,698 A | 2/1997 | Roberts et al. | |
| 5,662,702 A * | 9/1997 | Keranen | 623/1.23 |
| 5,667,522 A | 9/1997 | Flomenbilt et al. | |
| 5,690,644 A | 11/1997 | Yurek et al. | |
| 5,695,499 A | 12/1997 | Helgrson et al. | |
| 5,702,418 A | 12/1997 | Ravenscroft | |
| 5,746,692 A | 5/1998 | Bacich et al. | |
| 5,782,838 A | 7/1998 | Beyar et al. | |
| 5,817,102 A | 10/1998 | Johnson et al. | |
| 5,824,058 A | 10/1998 | Ravenscroft et al. | |
| 5,833,694 A | 11/1998 | Poncet | |
| 5,902,333 A | 5/1999 | Roberts et al. | |
| 5,984,964 A | 11/1999 | Roberts et al. | |
| 5,992,000 A * | 11/1999 | Humphrey et al. | 29/516 |
| 6,019,778 A | 2/2000 | Wilson et al. | |
| 6,086,528 A | 7/2000 | Adair | |
| 6,120,535 A | 9/2000 | McDonald et al. | |
| 6,156,055 A * | 12/2000 | Ravenscroft | 606/206 |
| 6,162,231 A | 12/2000 | Mikus et al. | |
| 6,203,550 B1 | 3/2001 | Olson | |
| 6,221,081 B1 * | 4/2001 | Mikus et al. | 606/108 |
| 6,238,430 B1 | 5/2001 | Klumb et al. | |
| 6,299,622 B1 | 10/2001 | Snow et al. | |
| 6,302,906 B1 | 10/2001 | Goicoechea et al. | |
| 6,322,586 B1 | 11/2001 | Monroe et al. | |
| 6,325,790 B1 | 12/2001 | Trotta | |
| 6,338,724 B1 * | 1/2002 | Dossa | 604/8 |
| 6,369,355 B1 | 4/2002 | Saunders | |
| 6,375,676 B1 | 4/2002 | Cox | |
| 6,451,025 B1 | 9/2002 | Jervis | |
| 6,514,280 B1 * | 2/2003 | Gilson | 623/1.11 |
| 6,517,569 B2 | 2/2003 | Mikus et al. | |
| 6,569,085 B2 | 5/2003 | Kortenbach et al. | |
| 6,607,551 B1 | 8/2003 | Sullivan et al. | |
| 6,623,491 B2 | 9/2003 | Thompson | |
| 6,656,211 B1 | 12/2003 | DiCaprio | |
| 6,656,214 B1 | 12/2003 | Fogarty et al. | |
| 6,663,660 B2 | 12/2003 | Dusbabek et al. | |
| 6,663,880 B1 | 12/2003 | Roorda et al. | |
| 6,669,716 B1 | 12/2003 | Gilson et al. | |
| 6,669,718 B2 | 12/2003 | Besselink | |
| 6,669,720 B1 | 12/2003 | Pierce | |
| 6,673,101 B1 | 1/2004 | Fitzgerald et al. | |
| 6,676,692 B2 * | 1/2004 | Rabkin et al. | 623/1.11 |
| 6,676,693 B1 | 1/2004 | Belding et al. | |
| 6,689,157 B2 | 2/2004 | Madrid et al. | |
| 6,695,809 B1 | 2/2004 | Lee | |
| 6,695,812 B2 | 2/2004 | Estrada et al. | |
| 6,695,862 B2 | 2/2004 | Cox et al. | |
| 6,699,274 B2 | 3/2004 | Stinson | |
| 6,699,277 B1 | 3/2004 | Freidberg et al. | |
| 6,702,849 B1 | 3/2004 | Dutta et al. | |
| 6,702,850 B1 | 3/2004 | Byun et al. | |
| 6,723,071 B2 | 4/2004 | Gerdts et al. | |
| 6,723,113 B1 | 4/2004 | Shkolnik | |
| 6,726,712 B1 | 4/2004 | Raeder-Devens et al. | |
| 6,733,521 B2 | 5/2004 | Chobotov et al. | |
| 6,736,828 B1 | 5/2004 | Adams et al. | |
| 6,743,219 B1 | 6/2004 | Dwyer et al. | |
| 6,746,423 B1 | 6/2004 | Wantink | |
| 6,749,627 B2 | 6/2004 | Thompson et al. | |
| 6,752,819 B1 | 6/2004 | Brady et al. | |
| 6,752,825 B2 | 6/2004 | Eskuri | |
| 6,755,855 B2 | 6/2004 | Yurek et al. | |
| 6,761,703 B2 | 7/2004 | Miller et al. | |
| 6,761,708 B1 | 7/2004 | Chiu et al. | |
| 6,761,733 B2 | 7/2004 | Chobotov et al. | |
| 6,773,446 B1 | 8/2004 | Dwyer et al. | |
| 6,773,447 B2 | 8/2004 | Laguna | |
| 6,773,448 B2 | 8/2004 | Kusleika et al. | |
| 6,774,157 B2 | 8/2004 | DelMain | |
| 6,780,182 B2 | 8/2004 | Bowman et al. | |
| 6,780,199 B2 | 8/2004 | Solar et al. | |
| 6,786,918 B1 | 9/2004 | Krivoruchko et al. | |
| 6,790,220 B2 | 9/2004 | Morris et al. | |
| 6,790,223 B2 | 9/2004 | Reever | |
| 6,800,081 B2 | 10/2004 | Parodi | |
| 6,802,846 B2 | 10/2004 | Hauschild et al. | |
| 6,802,849 B2 | 10/2004 | Blaeser et al. | |
| 6,805,702 B1 | 10/2004 | Chen et al. | |
| 6,805,703 B2 * | 10/2004 | McMorrow | 623/1.11 |
| 6,808,529 B2 | 10/2004 | Fulkerson | |
| 6,843,802 B1 | 1/2005 | Villalobos et al. | |
| 6,860,898 B2 | 3/2005 | Stack et al. | |
| 6,899,727 B2 | 5/2005 | Armstrong et al. | |
| 6,911,039 B2 | 6/2005 | Shiu et al. | |
| 6,942,674 B2 | 9/2005 | Belef et al. | |
| 6,953,475 B2 | 10/2005 | Shaolian et al. | |
| 6,972,054 B2 | 12/2005 | Kerrigan | |
| 6,984,244 B2 | 1/2006 | Perez et al. | |
| 6,989,024 B2 | 1/2006 | Hebert et al. | |
| 7,011,675 B2 | 3/2006 | Hemerick et al. | |
| 7,044,134 B2 * | 5/2006 | Khairkhahan et al. | 128/887 |
| 2001/0056295 A1 | 12/2001 | Solem | |
| 2002/0161425 A1 | 10/2002 | Hemerick et al. | |
| 2002/0183763 A1 | 12/2002 | Callot et al. | |
| 2002/0183826 A1 | 12/2002 | Dorn | |
| 2003/0144671 A1 | 7/2003 | Brooks et al. | |

FOREIGN PATENT DOCUMENTS

| | | |
|---|---|---|
| DE | 91 16 881.3 | 8/1994 |
| DE | 10148185 | 8/2005 |
| EP | 0 516 189 | 12/1992 |
| EP | 775470 | 3/1999 |
| EP | 1429684 | 7/2009 |
| JP | 2001-299932 | 10/2001 |
| WO | WO 97/14456 | 4/1997 |
| WO | WO 97/40739 | 11/1997 |
| WO | WO98/20812 | 5/1998 |
| WO | WO02/060345 | 8/2002 |
| WO | WO 02/083038 | 10/2002 |
| WO | WO03/034943 | 5/2003 |

OTHER PUBLICATIONS

Response to Office Action for EP1429684 dated Jun. 11, 2008.
International Search Report for WO2003/034943 dated Oct. 29, 2002 (included in publication of WO2003/034943).

* cited by examiner

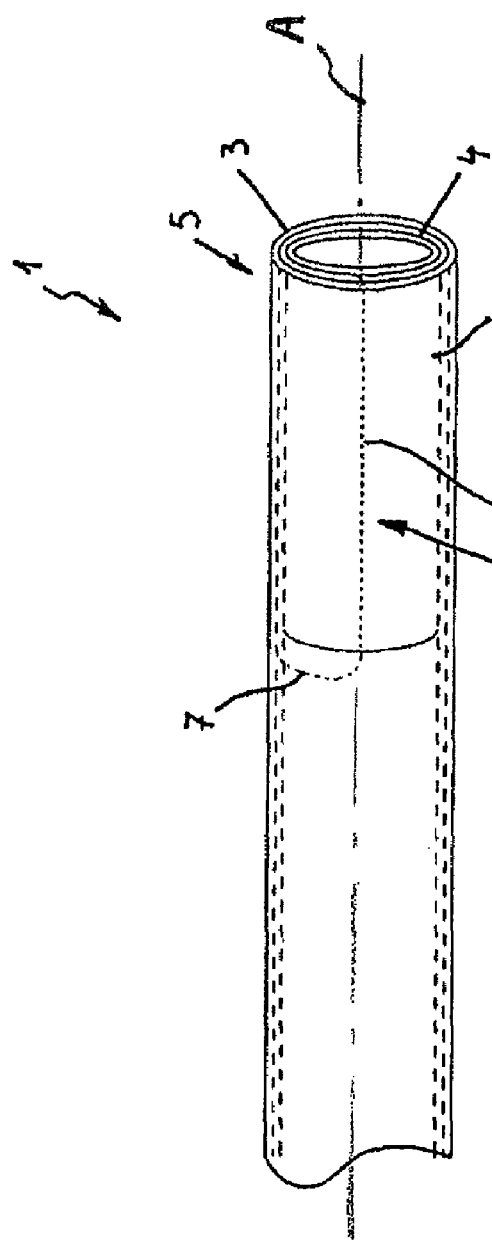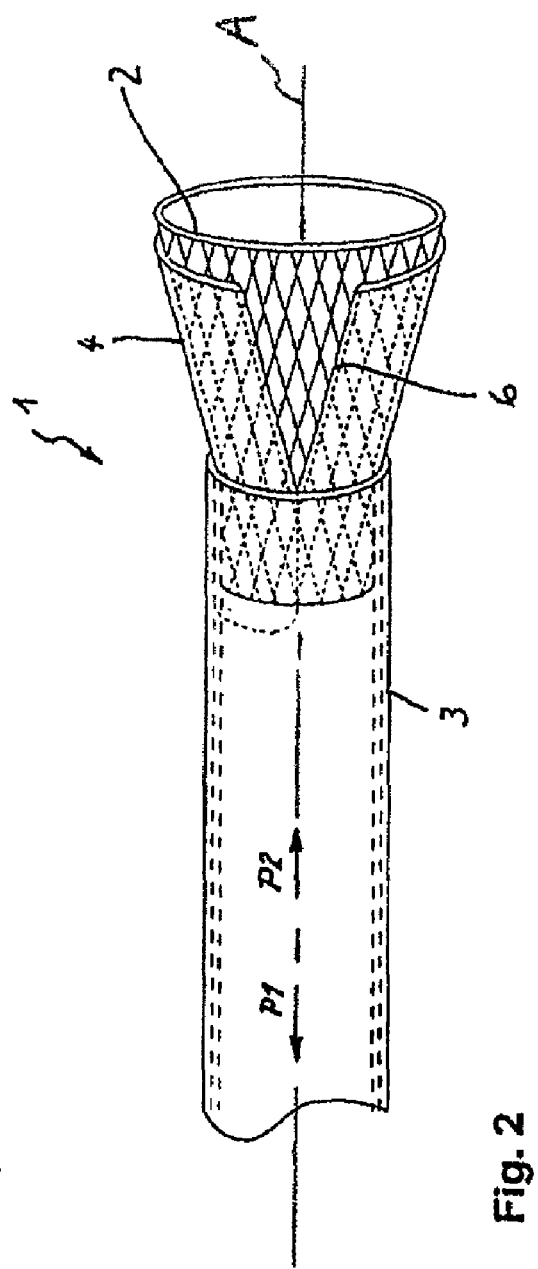
Fig. 1
Fig. 2

INSTRUMENT FOR IMPLANTING VASCULAR PROSTHESES

BACKGROUND OF THE INVENTION

The invention relates to an instrument for implanting expandable cylindrical vascular prostheses, so called stents or endoprostheses. The instrument includes a flexible outer tube and an inner tube arranged therein, with the outer and inner tubes moveable relative to one another.

Blockages of a vessel and constrictions of tubular body lumens, such as for example windpipe, bronchial tubes, esophagus, bile ducts, urinary tracts, blood vessels or the like, can be opened by surgical and non-surgical procedures. Non-surgical procedures involve the insertion of stents or endoprostheses in the area of the stenosis. Stents or endoprostheses are vascular supports which strengthen the inner vessel wall and are introduced through catheter technique into the vessel. Endoprostheses are referred to as ensheathed stents. In the following, the term stent is used consistently.

Stents are available in a wide variety of different plastic, metal and hybrid constructions. Many have fixed end diameters and are self-expanding (DE 91 16 881 U1 or DE 42 40 177 A1).

Other designs involve the option to change the diameter through application of suitable tools, e.g. balloons or expanders to suit the anatomic situation. Such a stent is disclosed in U.S. Pat. No. 5,201,901.

Further known in the art are stents made of so-called shape memory alloy. A shape memory alloy is, for example, nitinol which involves a nickel-titanium alloy, and has two defined states that are temperature-dependent. After pre-treatment, nitinol is martensitic in cold state, i.e. plastically deformable without relevant elastic restoring force. When heated, it changes to an austenitic elastic state. This shape memory characteristic is exploited for self-expansion of the stent.

Various tools and instruments are also known for implanting stents. U.S. Pat. No. 4,580,568 discloses a conventional instrument by which a stent is held together, when inserted in a tube. The stent is freed with the aid of a pusher and positioned. Positioning of the stent in the stenosis is, however, rather difficult because a precise placement of the stent in the stenosis requires a sensitive withdrawal of the instrument as the stent is freed. The stent may hereby shift or even spring away. A recovery of the stent into the instrument during implantation is not possible.

U.S. Pat. No. 5,158,548 proposes the arrangement of the stent at the end of a catheter which is held by a flexible sheath which can be removed by actuating a wire guided in the catheter (see in particular FIGS. 16 to 18). Also this type of instrument does not allow a correction or reversal of the procedure during implantation.

Depending on the design, known instruments for implanting vascular prostheses satisfy their function more or less satisfactorily. There is, however, a desire to enable a positional correction of the stent to a retrieval of the stent into the instrument in vivo during implantation.

Another problem that should be mentioned here relates to the fact that the instruments are normally pre-loaded with a stent. The stents are hereby held compressed within the instrument until implantation. Thus, the material of the self-expanding stent can fatigue with time and loose their spring force so that their function is adversely affected. For that reason, the instruments may not be used after their expiration date.

SUMMARY OF THE INVENTION

Starting from the state of the art, the invention is based on the object to provide an instrument with improved function for implanting vascular prostheses, which instrument ensures a very good placement of a vascular prosthesis in the body lumen and affords the possibility to re-compress and retrieve the vascular prosthesis so long as it has not yet fully exited the instrument.

This object is attained according to the invention by an instrument for implanting expandable cylindrical vascular prostheses, in particular stents or endoprostheses, which instruments includes an outer tube and an inner tube which are moveable relative to one another, wherein the inner tube is longitudinally slotted on the distal end, at least in an area thereof, and ensheathes the vascular prosthesis with this area which includes a longitudinal slot.

The instrument has an outer tube and an inner tube which are moveable relative to one another. The gist of the invention is the provision to slit the inner tube, at least in an area thereof, on the distal end in a longitudinal direction and to ensheath the vascular prosthesis with this area. In this situation, the inner tube is stabilized together with the contained compressed vascular prosthesis by the outer tube.

The stent can be introduced in the stenosis with the aid of the instrument. Placement of the stent is realized by withdrawing the outer tube. This process can be carried out gently and controlled. The spring force of the stent opens the inner tube laterally along the longitudinal slot and the stent is able to expand at this location. As the outer tube is retracted, the gradual expansion of the stent continues so that a controlled implantation is involved here. On the other hand, the stent can be retrieved again so long as it has not yet exited the instrument by pushing the outer tube forward. As a result, the inner tube constricts and compresses the stent.

Only when the outer tube has been retracted over the entire length of the stent, the stent expands fully deployed and is liberated. The predominantly lateral exiting motion of the stent in the stenosis site prevents the stent from shifting behind or in front of the constriction or even from springing. As a result, the stent can be accurately deployed, without longitudinal misalignment.

The inner and outer tubes may be made of same material or of different materials. In practice, tubes of Teflon have been used. Preferably, the inner tube is slotted at the distal end in the region in which it receives the stent. It is, however, generally possible to provide the inner tube along its entire length with a longitudinal slot.

According to a particularly advantageous configuration of the basic inventive concept involves the provision of a circular slot which follows the longitudinal slot and extends about a portion of the circumference of the inner tube. This measure supports the lateral expulsion of a vascular prosthesis.

According to another feature of the invention, there is provided a loading aid at one end of the outer tube for radial constriction of a vascular prosthesis disposed in the inner tube. The loading aid supports loading of an instrument with a stent and simplifies the procedure. Such a loading aid may be configured, for example, in the form of a funnel piece. It may be detachably or non-detachably associated to the end of the outer tube. The stent is positioned in the area of the inner tube, which area has the longitudinal slot. Subsequently, the outer tube is placed with the loading aid over the inner tube.

The loading aid constricts the inner tube and thereby compresses the stent until the latter is held completely in the instrument. The terminology in the art for this process is called "crimping". Thereafter, the loading aid can be removed. The loading process is simple and the risk of damage to the vascular prosthesis during loading is basically eliminated. In this way, a stent can be loaded into the instrument even immediately prior to use so that the risk of aging and material fatigue of the stent are prevented.

When using nitrinol vascular prostheses, it may be suitable to make the loading aid coolable. The vascular prosthesis can then be cooled by the loading aid. As a consequence of the cooling effect, the stent is small and rigid so as to allow easy installation into the instrument.

BRIEF DESCRIPTION OF THE DRAWING

Exemplary embodiments of the invention will now be described in detail with reference to the drawings, in which:

FIG. 1 shows the distal end of an instrument according to the invention with accommodated stent;

FIG. 2 shows a position of the instrument during implantation while the stent is partially expanded.

DETAILED DESCRIPTION OF PREFERRED EMBODIMENTS

Figure 3:
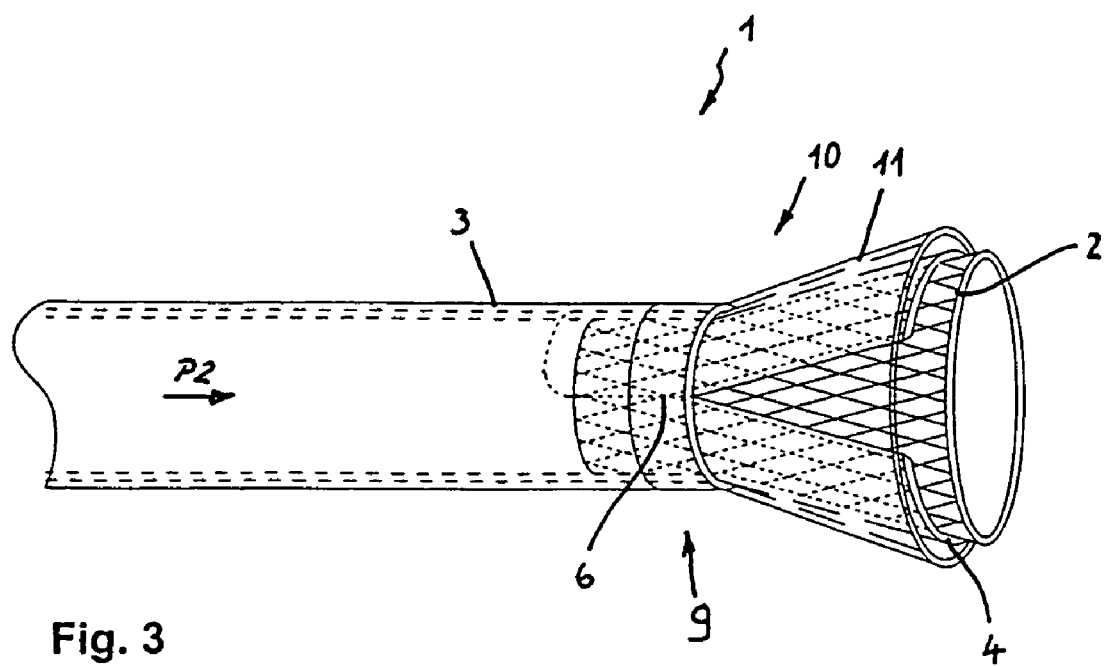
FIG. 3 shows the illustration of an instrument during loading with a stent.

FIG. 1 shows an instrument 1 according to the invention with a contained stent 2. The instrument 1 includes an outer tube 3 and an inner tube 4. Both tubes 3, 4 are made of flexible material such as Teflon and are moveable relative to one another.

The inner tube 4 includes at its distal end a longitudinal slot 6. The longitudinal slot 6 terminates in a circular slot 7 which extends over a portion of the circumference of the inner tube 4. The longitudinal slot 6 extends substantially parallel to the longitudinal axis A of the inner tube 4, while the circular slot 7 extends substantially perpendicular to the longitudinal axis A. The stent 2 is received in this longitudinally slotted area 8 of the inner tube 4.

The stent 2 is compressed in the initial position before implantation and is enveloped by the inner tube 4. The outer tube 3 closes in this situation the inner tube 4 and the stent 2 so as to render an expansion of the stent 2 impossible.

FIG. 2 shows the implantation while the stent 2 has not yet fully expanded. After the stent 2 has been brought into the stenosis site with the aid of the instrument 1, the implantation is carried out by retracting the outer tube 3 in relation to the inner tube 4. This movement is indicated by the arrow P1.

The spring force of the stent 2 pushes the inner tube 4 open laterally along the longitudinal slot 6, and the stent 2 is able to partially distend. If need be, the stent can be compressed again by pushing the outer tube 3 forwards (arrow P2). This is especially of advantage when a change of the intended installation position has occurred during implantation as a result of a muscle contraction caused, for example, by coughing or the like.

Only when the outer tube 3 has been withdrawn over the entire length of the stent 2, is it possible for the stent to fully expand. This expansion motion is predominantly lateral. The stent 2 can be precisely deployed, without longitudinal misalignment. The stent 2 thus rests laterally against the inner vessel wall in the stenosis site. In this way, the stent 2 can be precisely deployed. Risk of shift or sliding of the stent 2 is slight.

The illustration of FIG. 3 shows an instrument 1 in which a loading aid 10 in the form of a funnel piece 11 is arranged at one end 9 of the outer tube 3. The loading aid 10 is pushed together with the outer tube 3 over the inner tube 4. The stent 2 is located in the area 8 and may already be pre-compressed manually.

The loading aid progressively constricts the inner tube 4 in the area 8. As a result, the stent 2 is compressed. As the loading aid 10 and the outer tube 3 are advanced further, the stent 2 is received completely in the instrument 1.

The loading aid 10 may be an integral component of the outer tube 3. Following the loading process, the loading aid 10 is detached from the outer tube 3. Of course, it is also possible, to provide the loading aid 10 as a separate component. The outer tube 3 is then guided immediately behind the loading aid 10 during the loading process.

In practice, an instrument 1 according to the invention can be so configured that the loading aid 10 is designed as funnel-shaped enlargement of the proximal end of the outer tube 3. When the instrument 1 has to be reloaded during implantation, this can be implemented by reversing the outer tube 3, removed from the inner tube 4, so that the loading aid 10 now leads and pushing it over the inner tube 4 until the stent 2 is constricted on the distal end and positioned.

Suitably, the ends of the outer tube 2 and the inner tube 4 are rounded for facilitating the introduction during implantation.

What is claimed is:

1. An instrument for implanting an expandable cylindrical prosthesis, in particular a stent or an endoprosthesis, comprising an outer tube and an inner tube which are moveable relative to one another, wherein the inner tube has a distal end which includes a slot having a first portion extending in a proximal-distal direction adjacent the distal end of the inner tube and a second portion that extends in a circumferential direction about the inner tube, wherein at least a portion of the first portion extends substantially parallel to a longitudinal axis of the inner tube and at least a portion of the second portion extends substantially perpendicular to the longitudinal axis of the inner tube, and wherein the outer tube is configured to be retracted relative to the inner tube to deploy the prosthesis such that said slot of the inner tube is configured to distend as the prosthesis expands and is deployed from the outer tube.

2. The instrument of claim 1 and further comprising a loading aid is provided on one end of the outer tube for radial constriction of the prosthesis disposed in the inner tube.

3. The instrument of claim 2, wherein the loading aid is constructed so as to be coolable.

4. The instrument of claim 1, wherein at least a portion of the first portion extends substantially parallel to a longitudinal axis of the inner tube and at least a portion of the second portion extends substantially perpendicular to the longitudinal axis of the inner tube when the inner tube is completely disposed within the outer tube.

5. An instrument for implanting an expandable prosthesis, comprising an outer tube and an inner tube which are moveable relative to one another, said inner tube including a slot having a first portion extending in a proximal-distal direction adjacent a distal end of the inner tube and a second portion extending in a circumferential direction about the inner tube along a predetermined length to define an area for receiving a prosthesis, wherein at least a portion of the first portion extends substantially parallel to a longitudinal axis of the inner tube and at least a portion of the second portion extends substantially perpendicular to the longitudinal axis of the inner tube, and wherein the outer tube is configured to be retracted relative to the inner tube to deploy the prosthesis such that said slot of the inner tube is configured to distend as the prosthesis expands and is deployed from the outer tube.

6. The instrument of claim 5, and further comprising a loading aid provided on one end of the outer tube for radial constriction of the prosthesis in the inner tube.

7. The instrument of claim 6, wherein the loading aid is constructed so as to be coolable.

8. The instrument of claim 6, wherein the outer tube has a funnel-shaped configuration.

9. The instrument of claim 6, wherein the loading aid is an integral part of the outer tube.

10. The instrument of claim 6, wherein the loading aid is a separate part from the outer tube.

11. The instrument of claim 5, wherein the inner and outer tubes are made of flexible material.

12. The instrument of claim 5, wherein the inner and outer tubes are made of Teflon.

13. A method of deploying a prosthesis in a lumen of a person's body, comprising the steps of:
   a) placing a prosthesis in an inner tube of a delivery instrument;
   b) moving an outer tube of the delivery instrument over the inner tube to compress the inner tube and the contained prosthesis;
   c) positioning the delivery instrument in a region of a stenosis;
   d) retracting the outer tube relative to the inner tube to thereby allow the prosthesis to expand and to thereby distend the inner tube on one side along a slot formed in the inner tube, wherein the slot includes a first portion extending in a proximal-distal direction adjacent the distal end of the inner tube and a second portion extending in a circumferential direction about the inner tube, wherein at least a portion of the first portion extends substantially parallel to a longitudinal axis of the inner tube and at least a portion of the second portion extends substantially perpendicular to the longitudinal axis of the inner tube; and
   e) continuing retraction of the outer tube until the prosthesis is fully expanded.

14. The method of claim 13, and further comprising the step of pushing the outer tube relative to the inner tube before step e) to re-compress the prosthesis.

\* \* \* \* \*